United States Patent [19]

Durant et al.

[11] 4,170,652

[45] Oct. 9, 1979

[54] HETEROCYCLIC-METHYLTHIOALKYL-GUANIDINES

[75] Inventors: Graham J. Durant; Charon R. Ganellin, both of Welwyn Garden City; Rodney C. Young, Bengeo, all of England

[73] Assignee: Smith Kline & French Laboratories Limited, Welwyn Garden City, United Kingdom

[21] Appl. No.: 896,848

[22] Filed: Apr. 17, 1978

Related U.S. Application Data

[62] Division of Ser. No. 794,178, May 5, 1977, Pat. No. 4,107,319, which is a division of Ser. No. 551,220, Feb. 19, 1975, Pat. No. 4,036,971.

[30] Foreign Application Priority Data

Mar. 12, 1974 [GB] United Kingdom ............... 10869/74

[51] Int. Cl.$^2$ .................. C07D 213/53; C07D 249/08; A61K 31/44; A61K 31/41
[52] U.S. Cl. .................................... 424/263; 546/261; 546/264; 546/276; 424/269; 548/269
[58] Field of Search .................... 260/294.8 G, 308 R; 424/263, 269; 546/261, 264, 276

[56] References Cited

U.S. PATENT DOCUMENTS

| | | | |
|---|---|---|---|
| 4,034,101 | 7/1977 | Durant et al. | 424/273 |
| 4,049,671 | 9/1977 | Durant et al. | 260/308 R |
| 4,093,621 | 6/1978 | Brown et al. | 260/294.8 H |
| 4,098,898 | 7/1978 | Durant et al. | 424/273 R |
| 4,109,003 | 8/1978 | Durant et al. | 424/273 R |
| 4,120,966 | 10/1978 | Brown et al. | 424/263 |

*Primary Examiner*—Alan L. Rotman
*Attorney, Agent, or Firm*—Joan S. Keps; Richard D. Foggio; William H. Edgerton

[57] ABSTRACT

The compounds are N-(heterocyclomethylthioalkyl)-derivatives of alkylguanidines, C-alkyl and C-aryl amidines and S-alkylisothioureas. The compounds may also have N'-lower alkyl or N'-(heterocyclomethylthioalkyl)substituents. Three compounds of the invention are S-methyl-N-[2-(5-methyl-4-imidazolylmethylthio)ethyl]isothiourea, N,N'-bis-[2-(5-methyl-4-imidazolylmethylthio)ethyl]acetamidine, N,N'-bis-[2-(5-methyl-4-imidazolylmethylthio)ethyl]N''-methylguanidine. The compounds of this invention are histamine $H_2$-antagonists.

7 Claims, No Drawings

HETEROCYCLIC-METHYLTHIOALKYL-GUANIDINES

This is a division of application Ser. No. 794,178 filed May 5, 1977, U.S. Pat. No. 4,107,319 which is a division of application Ser. No. 551,220 filed Feb. 19, 1975, now U.S. Pat. No. 4,036,971.

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compound.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine is a typical example, and diphenhydramine and chlorpheniramine are other examples, are mediated through histamine $H_1$-receptors (Ash and Schild, *Brit. J. Pharmac. Chemother.*, 27, 427, (1966)). However, other of the biological actions of histamine are not inhibited by "antihistamines" and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure; in the treatment of certain conditions, for example inflammation and in inhibiting the actions of histamine on blood pressure, a combination of histamine $H_1$- and $H_2$-antagonists is useful. The compounds of this invention are histamine $H_2$-antagonists. These compounds are represented by the following formula:

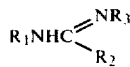

FORMULA I wherein $R_1$ represents a grouping of the structure shown in Formula II:

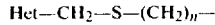

FORMULA II wherein Het is a nitrogen containing 5 or 6 membered heterocyclic ring selected from imidazole, pyridine, thiazole, isothiazole, thiadiazole, isoxazole and triazole which is optionally substituted by lower alkyl, hydroxyl, halogen or amino: n is 2 or 3: $R_2$ is lower alkyl, phenyl optionally substituted by hydroxy or mercapto, $SR_4$ or, when $R_3$ is other than hydrogen, $NHR_5$: $R_3$ is hydrogen, lower alkyl or $R_1$: $R_4$ and $R_5$ which may be the same or different are lower alkyl: and $R_3$ may be linked with $R_4$ or $R_5$ to form an additional 5-membered ring such as thiazoline or imidazoline, or a pharmaceutically acceptable acid addition salt.

Throughout the present specification and claims, by the term "lower alkyl" we mean an alkyl group containing from 1 to 4 carbon atoms, preferably methyl.

It will be understood that the structure illustrated in Formula I is only one of several representations and that other tautomeric forms are also covered by the present invention.

In a preferred group of compounds n is 2 and it is particularly preferably that Het is imidazole, optionally substituted by methyl or halogen; thiazole; or isothiazole or pyridine optionally substituted by methyl, hydroxyl or halogen. Halogen is preferably chloro or bromo.

Useful series of compounds are (a) that wherein $R_3$ is identical to $R_1$, (b) that wherein $R_2$ is lower alkylamino and (c) that wherein $R_2$ is lower alkylthio. Examples of specific compounds falling within the scope of the present invention are:

S-methyl-N-[2-(5-methyl-4-imidazolylmethylthio)ethyl]-isothiourea

N,N'-bis-[2-(5-methyl-4-imidazolylmethylthio)ethyl]acetamidine

N,N'-bis-[2-(5-methyl-4-imidazolylmethylthio)ethyl]-N''-methylguanidine.

The compounds of Formula I wherein $R_2$ is $SR_4$ and $R_4$ does not form an additional 5-membered ring may be prepared by alkylation of a thiourea of Formula III:

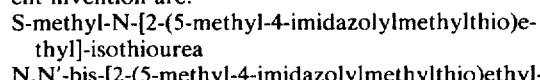

FORMULA III wherein $R_1$ and $R_3$ are as defined in Formula I to give an isothiourea of Formula IV

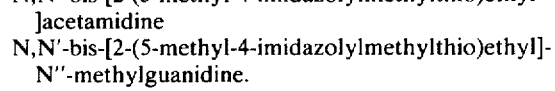

FORMULA IV wherein $R_4$ is lower alkyl. This reaction may be carried out conveniently using hydrogen chloride and the alcohol $R_4OH$, preferably at an elevated temperature near to the boiling point of the alcohol $R_4OH$. Alternatively the thiourea of Formula III may be alkylated using an alkyl halide, such as methyl iodide, or an alkylsulphate such as diethyl sulphate.

The compounds of Formula I other than those wherein $R_2$ is lower alkylthio may be prepared by treatment of a compound of Formula V

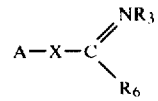

FORMULA V wherein $R_3$ is as defined in Formula I, $R_6$ is $R_2$ or $NHR_1$, $R_1$ and $R_2$ being as defined in Formula I except that $R_4$ when present is linked to $R_3$ to form a 5-membered ring such as a thiazoline ring, A is lower alkyl and X is oxygen when $R_6$ is lower alkyl or phenyl optionally substituted by hydroxy or mercapto, and X is sulphur when $R_6$ is $SR_4$, $NHR_5$, or $NHR_1$, with an amine of formula $R_7NH_2$, $R_7$ being $R_1$ when $R_6$ is $R_2$, and $R_7$ being lower alkyl when $R_6$ is $R_1NH$ and $R_3$ is other than hydrogen.

Examples of particular processes falling within the above general process are:

(a) The preparation of compounds of Formula VI

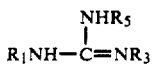

FORMULA VI wherein $R_1$, is as defined in Formula I, $R_3$ is lower alkyl or $R_1$ in which case the groups $R_1$ may be the same or different, and $R_5$ is lower alkyl and $R_3$ may be linked to $R_5$ to form a 5-membered ring, by treatment of an isothiourea of Formula IV wherein $R_3$ is $R_1$ with either a lower alkylamine or an amine of formula $R_1NH_2$.

(b) The preparation of compounds of Formula I, wherein $R_2$ is $SR_4$ and $R_3$ and $R_4$ are linked to form a 5-membered ring, by the reaction of $R_1NH_2$ with an S-lower alkylthiazoline of formula VII:

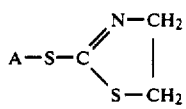

FORMULA VII wherein A represents a lower alkyl group.

(c) The preparation of compounds of Formula I wherein $R_2$ is lower alkyl or phenyl optionally substituted by hydroxy or mercapto by reaction of an amine of formula $R_1NH_2$ with an iminoether of Formula VII:

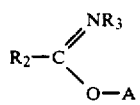

FORMULA VIII wherein A represents a lower alkyl group.

The iminoethers of Formula VIII wherein $R_3$ is hydrogen may be prepared by the reaction between a nitrile of formula $R_2CN$ and a lower alkanol AOH. The iminoethers of Formula VIII wherein $R_3$ is $R_1$ are generated by the reaction of an amine $R_1NH_2$ with an orthoester of formula $R_2$—C—$(OA)_3$.

Alternatively the compounds of Formula I wherein $R_2$ is mercaptophenyl may be prepared by treating the corresponding hydroxybenzamidine with phosphorus pentasulphide in a solvent such as pyridine.

The compounds of Formula I block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema test, where the oedema is induced by an irritant, the rat paw volume is reduced by subcutaneous injection of doses of a compound of Formula I. In a conventional test, such as the measurement of blood pressure in the anaesthetised cat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat of the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of the ion exchange resins to form the required salt either directly from the base or from a different addition salt.

Pharmaceutical compositions comprising a pharmaceutical carrier and a compound of Formula I or a pharmaceutically acceptable acid addition salt thereof and methods of blocking histamine $H_2$-receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regiment will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following examples wherein all temperatures are given in degrees Centigrade:

EXAMPLE 1

S-Methyl-N-[2-((5-methyl-4-imidazolyl)methylthio)ethyl]isothiourea hydriodide

A mixture of N-[2-((5-methyl-4-imidazolyl)methylthio)ethyl]thiourea (2.29 g) and methyl iodide (1.56 g) in acetone (45 ml) containing methanol (5 ml) was left at room temperature for 18 hours. Concentration followed by recrystallisation from isopropyl alcohol-petroleum ether (b.p. 60°/80°) gave the title compound (2.3 g) m.p. 128°–131°.

(Found: C, 28.8; H, 4.5; N, 14.8; S, 17.5; I, 33.8; $C_9H_{16}N_4S_2$ requires: C, 29.0; H, 4.6; N, 15.1; S, 17.2; I, 34.1%).

EXAMPLE 2

N,S-Dimethyl-N'-[2-((5-methyl-4-imidazolyl)methylthio)ethyl]isothiourea dihydriodide N-methyl-N'-[2-((5-methyl-4-imidazolyl)methylthio)ethyl]thiourea (10.0 g) was dissolved in methanol (400 ml) and 55% aqueous hydriodic acid (12.2 ml) was added, followed by methyl iodide (5.3 ml). The solution was heated under reflux for 4 hours and concentrated. The residue was dissolved in methanol (100 ml) and ether was added to afford the title product as the dihydriodide (5.48 g) m.p. 185°–186° (from isopropyl alcohol).

(Found: C, 23.4; H, 3.9; N, 10.9; I, 49.6; S, 12.6; $C_{10}H_{18}N_4S_2.2HI$ requires: C, 23.4; H, 3.9; N, 10.9; I, 49.4; S, 12.5%).

EXAMPLE 3

2-[2-(4-Imidazolylmethylthio)ethyl]amino-2-thiazoline hydriodide

A solution of 4(5)-[(2-aminoethyl)thiomethyl]imidazole (from the dihydrobromide (5.0 g) and excess potassium carbonate) and 2-methylthio-2-thiazoline hydriodide (4.09 g) in ethanol (100 ml) was heated under reflux for 21 hours. Following concentration the residue was crystallized from methanol-ether and then recrystallised from ethanol to give the title compound (2.9 g) m.p. 148.5°–150.5°.

(Found: C, 29.0; H, 4.0; N, 15.0; S, 17.5; I, 34.0; $C_9H_{14}N_4S_2.HI$ requires: C, 29.2; H, 4.1; N, 15.1; S, 17.5; I, 34.3%).

EXAMPLE 4

N-[2-(5-Methyl-4-imidazolylmethylthio)ethyl]benzamidine dihydrochloride

A solution of ethyl benzimidate hydrochloride (10.84 g) in water (25 ml) was basified with potassium carbonate (8.07 g) and extracted with diethyl ether (3×30 ml). The ethereal extracts were combined and dried over anhydrous potassium carbonate. The potassium carbonate was removed by filtration and the filtrate concentrated to about 30 ml. To the latter was added a solution of 4-methyl-5-[(2-aminoethyl)-thiomethyl]imidazole (5.00 g) in ethanol. The combined solutions were allowed to stand at room temperature for 6 days. The solution was concentrated to give an oil, cooled and acidified with ethanolic hydrogen chloride. The solution was concentrated and the residue recrystallised from isopropanol (with a trace of ether) to give N-[2-(5-methyl-4-imidazolylmethylthio)ethyl]benzamidine dihydrochloride (7.64 g) m.p. 221°–222.5° (from ethanol-ether).

(Found: C, 48.0; H, 5.9; N, 15.8; S, 9.1; $C_{14}H_{18}N_4S.2HCl$ requires: C, 48.4; H, 5.8; N, 16.1; S, 9.2%).

EXAMPLE 5

N-[2-(5-Methyl-4-imidazolylmethylthio)ethyl]-4-hydroxybenzamidine dihydrochloride.

4-Cyanophenol (11.91 g) was dissolved in dry diethyl ether (200 ml). Ethanol (10 ml) was added and the solution saturated with dry hydrogen chloride at 10°. The solution was stored at 0° over weekend. Yellow crystals of ethyl 4-hydroxybenzimidate hydrochloride (4.425 g) deposited. A solution of ethyl 4-hydroxybenzimidate hydrochloride (4.425 g) in water (10 ml) was basified with potassium carbonate (10.0 g) and extracted with diethyl ether (3×30 ml). This solution was dried over anhydrous potassium carbonate and added to a solution of 4-methyl-5-[(2-aminoethyl)thiomethyl]imidazole in dry ethanol (100 ml). Over 7 days at room temperature a crystalline solid was deposited. The crude base was recrystallised from ethanol-ether to give N-[2-(5-methyl-4-imidazolylmethylthio)ethyl]-4-hydroxybenzamidine as the ethanolate (2.12 g) m.p. 136°–138°. A sample of the ethanolate (1.58 g) was converted to the dihydrochloride by the addition of ethanolic hydrogen chloride. The solution was concentrated and the resulting solid recrystallised to give N-[2-(5-methyl-4-imidazolylmethylthio)ethyl]-4-hydroxybenzamidine. hydrochloride (1.28 g) (225.5°–228°).

(Found: C, 46.3; H, 5.6; N, 15.2; S, 8.8; Cl, 19.4; $C_{14}H_{18}N_4OS.2\,HCl$ requires: C, 46.3; H, 5.6; N, 15.4; S, 8.8; Cl, 19.5%).

EXAMPLE 6

N,N'-bis-[2-(5-Methyl-4-imidazolylmethylthio)ethyl]acetamidine trihydrochloride

A mixture of 4-methyl-5-[(2-aminoethyl)thiomethyl]imidazole (3.00 g), triethyl orthoacetate (1.42 g) and acetic acid (0.525 g) was refluxed for 60 minutes. The reaction mixture was allowed to cool, concentrated and dissolved in water. The aqueous solution was added to a solution of picric acid in boiling isopropanol. On cooling the crystalline picrate formed. This was recrystallised from isopropanol-water (3:1, 400 ml) to give N,N'-bis-[2-(5-methyl-4-imidazolylmethylthio)ethyl]acetamidine tripicrate (5.95 g) m.p. 205°–206°. The tripicrate was converted to the trihydrochloride by the addition of 5 N hydrochloric acid (50 ml) followed by extraction with toluene (5×30 ml). The aqueous solution was concentrated and the residual solid was boiled with isopropanol and gradually crystallised. The crude trihydrochloride was recrystallised from ethanol-ethyl acetate to give N,N'-bis-[2-(5-methyl-4-imidazolylmethylthio)ethyl]acetamidine trihydrochloride (1.89 g) m.p. 230°–232°.

(Found: C, 40.4; H, 6.2; N, 17.5; S, 13.2; Cl, 21.9. $C_{16}H_{26}N_6S_2.\,3\,HCl$ requires: C, 40.4; H, 6.1; N, 17.7; S, 13.5; Cl, 22.4%).

In a similar manner (a) N,N'-bis-[2-(3-bromo-2-pyridylmethylthio)ethyl]acetamidine may be prepared from 3-bromo-2-[(2-aminoethyl)thiomethyl]pyridine.

(b) N,N'-bis-[2-(2-thiazolylmethylthio)ethyl]acetamidine may be prepared from 2-[(2-aminoethyl)thiomethyl]thiazole.

(c) N,N'-bis-[2-(3-isothiazolylmethylthio)ethyl]acetamidine may be prepared from 3[(2-aminoethyl)thiomethyl]isothiazole.

(d) N,N'-bis-[2-(3-chloro-2-pyridylmethylthio)ethyl]acetamidine, may be prepared from 3-chloro-2-[(2-aminoethyl)thiomethyl]pyridine.

EXAMPLE 7

2-[2-((5-Methyl-4-imidazolyl)methylthio)ethyl]amino-2-imidazoline dihydrochloride A solution of 4-methyl-5-((2-aminoethyl)thiomethyl)imidazole (8.55 g) and 2-methylmercapto-2-imidazoline hydriodide (13.2 g) in ethanol (50 ml) was heated under reflux for 15 hours. The residue following concentration was dissolved in ethanol and treated with sodium picrate in hot ethanol. The picrate obtained on cooling was recrystallised from ethanol (16.5 g, m.p. 190°-192°) and treated with hydrochloric acid. Picric acid was removed by toluene extraction and the aqueous layer was concentrated and the residue recrystallised twice from isopropyl alcohol to give the title compound as the dihydrochloride (7.0 g) m.p. 189°-191°.

(Found: C, 38.6; H, 6.3; N, 22.3; S, 10.5; Cl, 22.6. $C_{10}H_{17}N_5S.2HCl$ requires: C, 38.5; H, 6.1; N, 22.4; S, 10.3; Cl, 22.7%).

EXAMPLE 8

N,N'-Dimethyl-N''-[2-(5-methyl-4-imidazolylmethylthio)ethyl]guanidine dihydrochloride N,N'S-Trimethylisothiouronium iodide (12.0 g) was converted into the sulphate by ion exchange on a resin on the $SO_4=$ form (IRA 401). The concentrated eluate of the sulphate was reacted directly with 4-methyl-5-((2-aminoethyl)thiomethyl)imidazole (6.85 g) at 70°-80° for 48 hours. Following concentration, the crude product was converted to a picrate (8 g, m.p. 110°-120° (from aqueous ethanol)). Following conversion to the hydrochloride and purification on an ion-exchange column (OH⁻ form) with elution by hydrochloric acid, the title compound, m.p. 260° (dec) was obtained.

EXAMPLE 9

S-Methyl-N,N'-bis-[2-((5-methyl-4-imidazolyl)methylthio)ethyl]isothiourea trihydrochloride (i) A solution of 4-methyl-5-((2-aminoethyl)thiomethyl) imidazole (34.0 g) and carbon disulphide (7.6 g) in ethanol (250 ml) was heated under reflux for 6 hours. Concentration followed by chromatographic purification of the product on a column of silica gel with elution by isopropyl alcohol-ethyl acetate followed by isopropyl alcohol-ethanol gave N,N'-bis-[2-(5-methyl-4-imidazolyl)methylthio)ethyl]thiourea (18 g), m.p. 133°-135°.

(Found: C, 47.0; H, 6.1; N, 22.0. $C_{15}H_{24}N_6S_3$ requires: C, 46.8; H, 6.3; N, 21.9%).

(ii) Dry hydrogen chloride was passed into a solution of N,N'-bis-[2-((5-methyl-4-imidazolyl)methylthio)ethyl]thiourea (7.7 g) in methanol at 80° for 5 hours. Concentration and re-evaporation with isopropyl alcohol afforded S-methyl-N,N'-bis-[2-((5-methyl-4-imidazolyl)methylthio)ethyl]isothiourea trihydrochloride (9.0 g), m.p. 212°-215° (isopropyl alcohol).

(Found: C, 37.6; H, 5.7; N, 16.3; S, 18.6; Cl, 20.5 $C_{16}H_{26}N_6S_3$. 3 HCl requires: C, 37.8; H, 5.8; N, 16.5; S, 18.9; Cl, 20.9%).

EXAMPLE 10

N,N'-bis-[2-((5-Methyl-4-imidazolyl)methylthio)ethyl]-N''-methylguanidine

A solution of N,N'-bis-[2-((5-methyl-4-imidazolyl)methylthio)ethyl]-S-methylisothiourea trihydrochloride (2.0 g) in 33% ethanolic methylamine (60 ml) was heated under reflux for 3 hours. The mixture was basified with sodium methoxide, filtered and the filtrate was concentrated under reduced pressure. Treatment of the residue with ethanolic picric acid afforded N,N'-bis-[2-((5-methyl-4-imidazolyl)methylthio)ethyl]-N''-methylguanidine tripicrate (2.8 g) m.p. 169°-170°.

(Found: C, 38.0; H, 3.4; N, 20.7; S, 6.0. $C_{16}H_{27}N_7S_2.3 C_6H_3N_3O_7$ requires: C, 38.2; H, 3.4; N, 21.0; S, 6.0%).

Treatment of the tripicrate with hydrochloric acid and removal of picric acid by extraction with toluene afforded the trihydrochloride.

In a similar manner N,N'-bis-[2-((5-methyl-4-imidazolyl)methylthio)ethyl]-N''-butylguanidine may be prepared using butylamine in ethanol in place of ethanolic methylamine.

EXAMPLE 11

N-[2-(5-Methyl-4-imidazolylmethylthio)ethyl]-4-mercaptobenzamidine (a) 4-Cyanothiophenol was treated with hydrogen chloride in ether at 0° and the hydrochloride salt produced was treated with potassium carbonate to give ethyl 4-mercaptobenzimidate. Ethyl 4-mercaptobenzimidate was treated with 4-methyl-5-[(2-aminoethyl)thiomethyl]imidazole in dry ethanol at room temperature to give the title product.

(b) N-[2-(5-Methyl-4-imidazolylmethylthio)ethyl]-4-hydroxybenzamidine and a slight excess of phosphorus pentasulphide were refluxed in pyridine for 45 minutes to give the title compound.

EXAMPLE 12

N-[2-(5-Methyl-4-imidazolylmethylthio)ethyl]acetamidine

A mixture of ethyl acetimidate and 4-methyl-5-[(2-aminoethyl)thiomethyl]imidazole in ethanol was allowed to stand at room temperature for 6 days. The mixture was concentrated, treated with ethanolic hydrogen chloride and evaporated to give the title product as the dihydrochloride.

EXAMPLE 13

Treatment of the following thioureas:

a. N-[2-(2-Pyridylmethylthio)ethyl]-N'-[2-((5-methyl-4-imidazolyl)methylthio)ethyl]thiourea.

b. N-[2-(3-Pyridylmethylthio)ethyl]-N'-[2-((5-methyl-4-imidazolyl)methylthio)ethyl]thiourea.

c. N,N'-bis[2-((3-hydroxy-2-pyridyl)methylthio)ethyl]thiourea.

d. N,N'-bis-[2-(3-isoxazolylmethylthio)ethyl]thiourea.

with hydrogen chloride in methanol according to the general procedure of Example 9 (ii) results in the formation of the S-methylisothioureas:

a. S-Methyl-N-[2-(2-pyridylmethylthio)ethyl]-N'-[2-((5-methyl-4-imidazolyl)methylthio)ethyl]isothiourea.

b. S-Methyl-N-[2-(3-pyridylmethylthio)ethyl]-N'-[2-((5-methyl-4-imidazolyl)methylthio)ethyl]isothiourea.

c. S-Methyl-N,N'-bis-[2-((3-hydroxy-2-pyridyl)methylthio)ethyl]isothiourea.

d. S-Methyl-N,N'-bis-[2-((3-isoxazolylmethylthio)ethyl]isothiourea.

and treatment of these S-methylisothioureas with methylamine according to the general procedure of Example 10 results in the formation of the N''-methylguanidines:

a. N-[2-(2-pyridylmethylthio)ethyl]-N'-[2-((5-methyl-4-imidazolyl)methylthio)ethyl]-N''-methylguanidine.

b. N-[2-(3-pyridylmethylthio)ethyl]-N'-[2-((5-methyl-4-imidazolyl)methylthio)ethyl]-N''-methylguanidine.

c. N,N'-bis-[2-((3-hydroxy-2-pyridyl)methylthio)ethyl]-N''-methylguanidine.

d. N,N'-bis-[2-(3-isoxazolyl-methylthio)ethyl]N''-methylguanidine.

EXAMPLE 14

Substitution of:
(a) 4-[(2-aminoethyl)thiomethyl]imidazole.
(b) 4-bromo-5-[(2-aminoethyl)thiomethyl]imidazole.
(c) 1-methyl-2-[(2-aminoethyl)thiomethyl]imidazole.
(d) 2-[(2-aminoethyl)thiomethyl]imidazole.
(e) 3-chloro-2-[(2-aminoethyl)thiomethyl]pyridine.
(f) 3-bromo-2-[(2-aminoethyl)thiomethyl]pyridine.
(g) 3-methyl-2-[(2-aminoethyl)thiomethyl]pyridine.
(h) 2-[(2-aminoethyl)thiomethyl]thiazole.
(i) 3-[(2-aminoethyl)thiomethyl]isothiazole.
(j) 5-amino-2-[(2-aminoethyl)thiomethyl]-1,3,4-thiadiazole.
(k) 3-[(2-aminoethyl)thiomethyl]-1,2,4-triazole.
(l) 4-[(3-(2-aminomethyl)thiopropyl]imidazole.

for 4-methyl-5-((2-aminoethyl)thiomethyl)imidazole in the general procedure of Example 9(i) followed by treatment of the product according to the general procedure of Examples 9(ii) results in the formation of the following S-methyl isothioureas.

a. S-methyl-N,N'-bis-[2-(4-imidazolyl methylthio)ethyl]isothiourea.

b. S-methyl-N,N'-bis-[2-(5-bromo-4-imidazolyl methylthio)ethyl]isothiourea.

c. S-Methyl-N,N'-bis-[2-(1-methyl-2-imidazolyl methylthio)ethyl]isothiourea.

d. S-Methyl-N,N'-bis-[2-(2-imidazolyl methylthio)ethyl]isothiourea.

e. S-Methyl-N,N'-bis-[2-(3-chloro-2-pyridyl methylthio)ethyl]isothiourea.

f. S-Methyl-N,N'-bis[2-(3-bromo-2-pyridyl methylthio)ethyl]isothiourea.

g. S-Methyl-N,N'-bis-[2-(3-methyl-2-pyridyl methylthio)ethyl]isothiourea.

h. S-Methyl-N,N'-bis-[2-(2-thiazolyl methylthio)ethyl]isothiourea.

i. S-Methyl-N,N'-bis-[2-(3-isothiazolyl methylthio)ethyl]isothiourea.

j. S-Methyl-N,N'-bis-[2-(5-amino-2-(1,3,4-thiadiazolyl)-methylthio)ethyl]isothiourea.

k. S-Methyl-N,N'-bis-[2-(3-(1,2,4-triazolyl)methylthio)ethyl]isothiourea.

l. S-Methyl-N,N'-bis-[3-(4-imidazolylmethylthio)propyl]isothiourea.

and treatment of these S-methyl isothioureas with methylamine according to the general procedure of Example 10 results in the formation of the following N''-methylguanidines:

a. N,N'-bis-[2-(4-imidazolyl methylthio)ethyl]-N''-methylguanidine.

b. N,N'-bis-[2-(5-bromo-4-imidazolyl methylthio)ethyl]-N''-methylguanidine.

c. N,N'-bis-[2-(1-methyl-2-imidazolyl methylthio)ethyl]-N''-methylguanidine.

d. N,N'-bis-[2-(2-imidazolyl methylthio)ethyl]-N''-methylguanidine.

e. N,N'-bis-[2-(3-chloro-2-pyridyl methylthio)ethyl]-N''-methylguanidine.

f. N,N'-bis-[2-(3-bromo-2-pyridyl methylthio)ethyl]-N''-methylguanidine.

g. N,N'-bis-[2-(3-methyl-2-pyridyl methylthio)ethyl]-N''-methylguanidine.

h. N,N'-bis-[2-(2-thiazolyl methylthio)ethyl]-N''-methylguanidine.

i. N,N'-bis-[2-(3-isothiazolyl methylthio)ethyl]-N''-methylguanidine.

j. N,N'-bis-[2-(5-amino-2-(1,3,4-thiadiazolyl)methylthio)ethyl]-N''-methylguanidine.

k. N,N'-bis-[2-(3-(1,2,4-triazolyl)methylthio)ethyl]-N''-methylguanidine.

l. N,N'-bis-[3-(4-imidazolylmethylthio)propyl]-N''-methylguanidine.

EXAMPLE 15

| Ingredients | Amounts |
| --- | --- |
| N,N'-bis-[2-(5-methyl-4-imidazolyl-methylthio)ethyl]N''-methylguanidine trihydrochloride. | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 16

| Ingredients | Amounts |
| --- | --- |
| N,N'-bis-[2-(5-methyl-4-imidazolyl-methylthio)ethyl]-N''-methylguanidine trihydrochloride. | 200 mg. |
| Lactose | 100 mg. |

The ingredients are screened, mixed and filled into a hard gelatin capsule.

What is claimed is:

1. A compound of the formula:

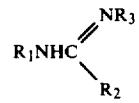

wherein $R_1$ represents a grouping of the structure

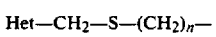

wherein Het is a nitrogen containing 5 or 6 membered heterocyclic ring selected from pyridine and 1,2,4-triazole which is optionally monosubstituted by lower alkyl, hydroxyl, halogen or amino; n is 2 or 3; $R_2$ is $NHR_5$; $R_3$ is $R_1$; and $R_5$ is lower alkyl, or a pharmaceutically acceptable acid addition salt thereof.

2. A compound according to claim 1 wherein Het is pyridine which is optionally monosubstituted by lower alkyl, hydroxyl, halogen or amino.

3. A compound according to claim 1 wherein n is 2.

4. A compound according to claim 1 wherein Het is pyridine optionally monosubstituted by methyl, hydroxyl or halogen.

5. A compound according to claim 1 wherein $R_3$ is identical to $R_1$.

6. A pharmaceutical composition to block histamine $H_2$-receptors comprising, in an effective amount to block said receptors, a compound of claim 1 in combination with a pharmaceutically acceptable diluent or carrier.

7. A method of blocking histamine $H_2$-receptors which comprises administering to an animal in need thereof, in an effective amount to block said receptors, a compound of claim 1.

* * * * *